(12) United States Patent
Berg et al.

(10) Patent No.: US 6,451,033 B1
(45) Date of Patent: Sep. 17, 2002

(54) TUBULAR MEDICAL GRAFT CONNECTORS

(75) Inventors: Todd Allen Berg, Lino Lakes, MN (US); Thomas J. Bachinski, Lakeville, MN (US); Alex Alden Peterson, Maple Grove, MN (US); Gregory Alan Boldenow, Crystal, MN (US)

(73) Assignee: St. Jude Medical ATG, Inc., Minneapolis, MN (US)

(*) Notice: Subject to any disclaimer, the term of this patent is extended or adjusted under 35 U.S.C. 154(b) by 0 days.

(21) Appl. No.: 09/921,048

(22) Filed: Aug. 2, 2001

Related U.S. Application Data

(60) Division of application No. 09/539,643, filed on Mar. 30, 2000, now Pat. No. 6,293,965, which is a division of application No. 09/293,254, filed on Apr. 16, 1999, now Pat. No. 6,152,945, which is a division of application No. 08/958,937, filed on Oct. 28, 1997, now Pat. No. 5,972,017, which is a continuation-in-part of application No. 08/839,199, filed on Apr. 23, 1997, now Pat. No. 6,036,702.

(51) Int. Cl.⁷ .................... A61B 17/08; A61B 17/00
(52) U.S. Cl. ........................ 606/153; 606/198
(58) Field of Search .................. 606/153, 151, 606/152, 108, 198, 191, 200; 623/1.15–1.2

(56) References Cited

U.S. PATENT DOCUMENTS

| | | |
|---|---|---|
| 4,214,587 A | 7/1980 | Sakura, Jr. |
| 4,470,415 A | 9/1984 | Wozniak |
| 4,503,569 A | 3/1985 | Dotter |
| 4,592,754 A | 6/1986 | Gupte et al. |
| 4,617,932 A | 10/1986 | Kornberg |
| 4,665,906 A | 5/1987 | Jervis |
| 4,728,328 A | 3/1988 | Hughes et al. |
| 4,787,899 A | 11/1988 | Lazarus |
| 4,897,077 A | 1/1990 | Cicciu et al. |
| 5,104,399 A | 4/1992 | Lazarus |
| 5,135,467 A | 8/1992 | Citron ................... 600/16 |
| 5,211,658 A | 5/1993 | Clouse |
| 5,211,683 A | 5/1993 | Maginot ................ 128/898 |
| 5,234,448 A | 8/1993 | Wholey et al. ......... 606/153 |
| 5,275,622 A | 1/1994 | Lazarus et al. |
| 5,304,220 A | 4/1994 | Maginot |
| 5,316,023 A | 5/1994 | Palmaz et al. ......... 128/898 |

(List continued on next page.)

FOREIGN PATENT DOCUMENTS

| | | | |
|---|---|---|---|
| AU | 670239 | 1/1994 | ......... A61F/2/06 |
| EP | 539237 A1 | 4/1993 | ......... A61F/2/06 |
| EP | 637 454 A1 | 2/1995 | ....... A61M/25/10 |
| EP | 680 734 A2 | 11/1995 | ......... A61F/2/06 |
| EP | 684 022 A2 | 11/1995 | ......... A61F/2/06 |
| EP | 686379 A2 | 12/1995 | ......... A61F/2/06 |
| EP | 712 614 A1 | 5/1996 | ......... A61F/2/06 |
| GB | 489316 | 7/1938 | |
| GB | 2269104 A | 2/1994 | ......... A61F/2/06 |
| WO | WO 93/00868 | 1/1993 | ......... A61F/2/06 |
| WO | WO 96/18361 | 6/1996 | ......... A61F/2/06 |
| WO | WO 96/22745 | 8/1996 | ......... A61F/2/06 |
| WO | WO 97/13463 | 4/1997 | ......... A61B/17/00 |
| WO | WO 97/13471 | 4/1997 | ......... A61B/19/00 |
| WO | WO 98/38939 | 9/1998 | ......... A61B/19/00 |

*Primary Examiner*—Olik Chaudhuri
*Assistant Examiner*—(Vikki) Hoa B. Trinh
(74) *Attorney, Agent, or Firm*—Fish & Neave; Robert R. Jackson; Laura A. Sheridan

(57) ABSTRACT

Connectors are provided for making connections between tubular conduits in medical procedures such as those involving treatment of a patient's circulatory system. The connectors are variously configured for making end-to-side or end-to-end connections of tubular conduits. One of the tubular conduits may be a graft conduit, which can be artificial conduit, natural conduit, or a combination of both. The connectors for making end-to-side connections can be generally T-shaped or L-shaped. Various portions of the connectors can attach to the inside or outside of the associated conduit, depending on the connector configuration that is selected.

18 Claims, 16 Drawing Sheets

U.S. PATENT DOCUMENTS

| | | |
|---|---|---|
| 5,354,336 A | 10/1994 | Kelman et al. |
| 5,387,235 A | 2/1995 | Chuter |
| 5,397,345 A | 3/1995 | Lazarus |
| 5,443,497 A | 8/1995 | Venbrux |
| 5,452,733 A | 9/1995 | Sterman et al. ............. 128/898 |
| 5,456,712 A | 10/1995 | Maginot |
| 5,489,295 A | 2/1996 | Piplani et al. |
| 5,507,769 A | 4/1996 | Marin et al. ................ 606/198 |
| 5,522,880 A | 6/1996 | Barone et al. |
| 5,545,214 A | 8/1996 | Stevens |
| 5,676,670 A | 10/1997 | Kim ........................... 606/108 |
| 5,695,504 A | 12/1997 | Gifford, III et al. ........ 606/153 |
| 5,697,948 A | 12/1997 | Marin et al. ................ 606/198 |
| 5,976,178 A | 11/1999 | Goldsteen |
| 6,001,124 A | 12/1999 | Bachinski |
| 6,036,702 A | 3/2000 | Bachinski et al. .......... 606/153 |
| 6,074,416 A | 6/2000 | Berg et al. |
| 6,120,432 A | 9/2000 | Sullivan et al. |
| 6,152,945 A * | 11/2000 | Bachinski et al. .......... 606/198 |
| 6,293,965 B1 * | 9/2001 | Berg et al. ................. 623/1.13 |

\* cited by examiner

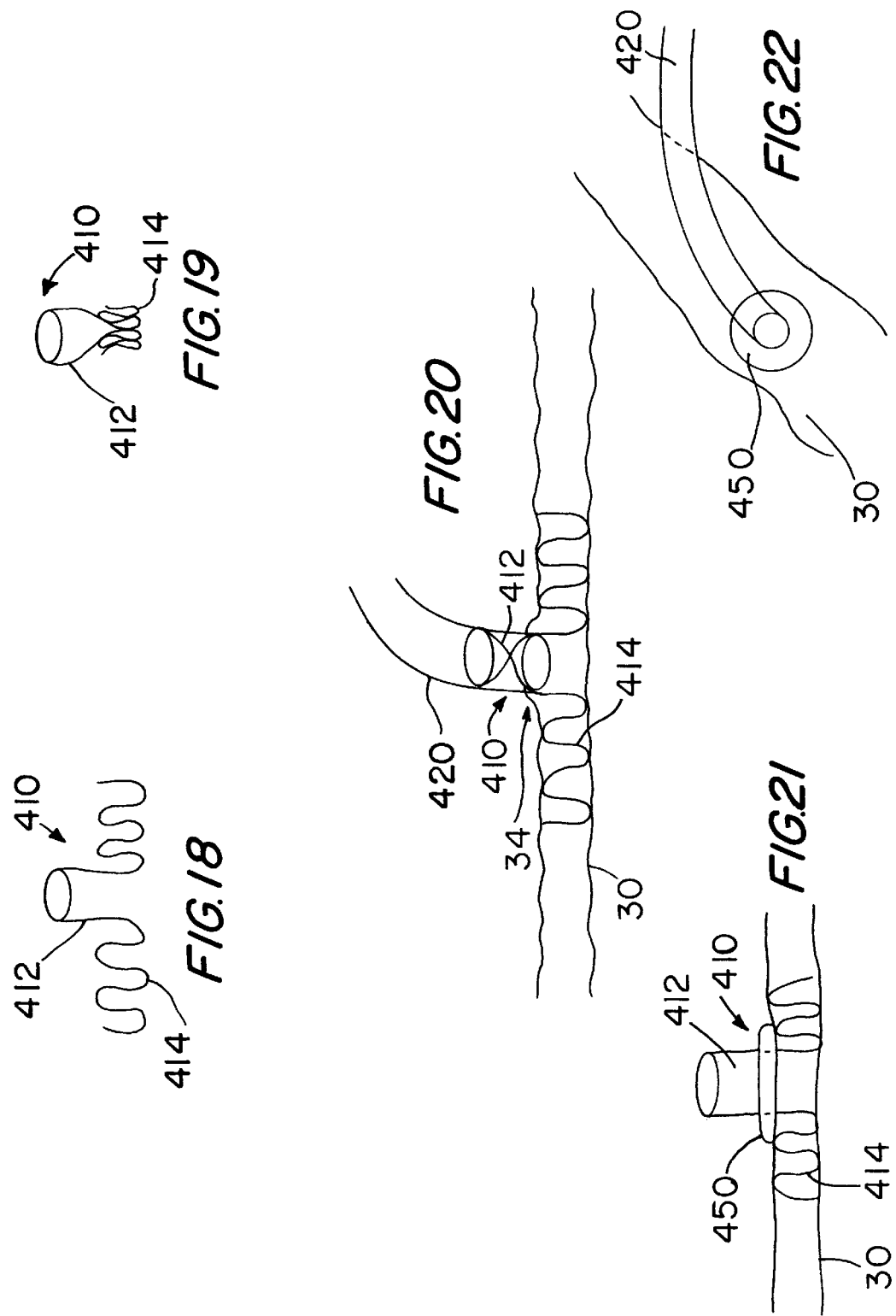

TUBULAR MEDICAL GRAFT CONNECTORS

This application is a division of application Ser. No. 09/539,643, filed Mar. 30, 2000, now U.S. Pat. No. 6,293,965 which is a division of application Ser. No. 09/293,254, filed Apr. 16, 1999 (now U.S. Pat. No. 6,152,945), which is a division of application Ser. No. 08/958,937 (now U.S. Pat. No. 5,972,017), filed Oct. 28, 1997, which is a continuation-in-part of application Ser. No. 08/839,199, filed Apr. 23, 1997 (now U.S. Pat. No. 6,036,702), all of which prior applications are hereby incorporated by reference herein in their entireties.

BACKGROUND OF THE INVENTION

This invention relates to tubular medical grafts, and more particularly to connectors for use in making tubular connections between tubular grafts and a patient's tubular tissue structures.

Goldsteen et al. U.S. Pat. No. 5,976,178, Sullivan et al. U.S. Pat. No. 6,120,432, and Sullivan et al. international publication No. WO 98/55027 (all of which are hereby incorporated by reference herein) show examples of medical procedures in which it is necessary to make one or more tubular connections between a patient's tubular body tissue structures and a tubular graft. The graft may be either natural body tissue relocated from elsewhere in the patient's body, an artificial graft structure, or a combination of natural and artificial structures. In the exemplary procedures shown in the three references mentioned above it is typically necessary to connect an end of the graft to a side wall of the patient's pre-existing body tubing, but it may also sometimes be necessary to connect an end of a graft to an end of a pre-existing body tube. The three references mentioned above deal primarily with procedures that are performed to the greatest extent possible percutaneously and through lumens of a patient's tubular body structures. Thus graft connectors are sometimes needed that can be delivered and installed via such lumens. At other times, however, graft connectors are needed that can be installed during more traditional surgical procedures.

It is important for graft connectors to be easy and quick to install (whether percutaneously or surgically), but to be secure after installation. It is typically preferred for a graft connector to be relatively flexible after installation so that it does not form an unnaturally rigid structure in the patient's body. Improvements are constantly sought in all of these aspects of graft connectors.

In view of the foregoing, it is an object of this invention to provide improved tubular graft connectors for making tubular connections between tubular grafts and a patient's tubular body tissue structures.

It is a more particular object of this invention to provide tubular graft connectors that are easy and quick to install, in some cases percutaneously and in some cases surgically, but which are strong and secure after installation.

SUMMARY OF THE INVENTION

These and other objects of the invention are accomplished in accordance with the principles of the invention by providing tubular graft connector structures that, for making end-to-side connections between an end of a graft and a side wall of a patient's tubular body structure, have a first tubular section for tubular attachment to the graft and a second tubular section transverse to the first section for tubular attachment to the patient's tubular body structure. The second section may extend transversely in only one direction from the first section, making a somewhat L-shaped connector. Or the second section may extend transversely in both directions from the first section, making a T-shaped connector. The second section may be adapted to fit concentrically within the patient's tubular body structure, with the first section extending from an aperture in the side wall of that body structure. The first section may be connected in advance to the end of the graft. For example, if the graft is or includes an artificial tubular structure, the first section may be integral with or otherwise attached to that artificial structure. Alternatively, if the graft is or includes a natural tubular structure, the first section may be tubularly connected either inside or outside of that structure.

Connector structures of this invention may include a substantially annular component which fits around an axial end portion of a graft conduit and which is circumferentially compressible to annularly engage that conduit. The annular component may have radially inwardly extending prongs for enhancing the engagement of the graft conduit. Resilient fingers may be resiliently biased to extend radially outward adjacent an axial end portion of the annular structure to retain the annular structure in an aperture in a side wall of a patient's pre-existing body conduit. Alternatively, for use in making an end-to-end connection, the connector structure may include a second substantially annular component similar to the first component for attachment to an end portion of a second body conduit similar to the attachment of the first component to the graft conduit.

The invention also includes certain methods and apparatus which can be used in the installation of graft connectors.

Further features of the invention, its nature and various advantages, will be more apparent from the accompanying drawings and the following detailed description of the preferred embodiments.

BRIEF DESCRIPTION OF THE DRAWINGS

FIG. 18 is a simplified elevational view of yet another illustrative embodiment of a graft connector in accordance with this invention.

FIG. 19 is another view similar to FIG. 18 showing another operating condition of the connector of FIG. 18.

FIG. 20 is another simplified elevational view, partly in section, showing a connector like the FIG. 18 connector in use.

FIG. 21 is another view similar to FIG. 20 with additional structure in accordance with the invention added.

FIG. 22 is a simplified perspective view of a structure like that shown in FIG. 21.

DETAILED DESCRIPTION OF THE PREFERRED EMBODIMENTS

Figure 1:
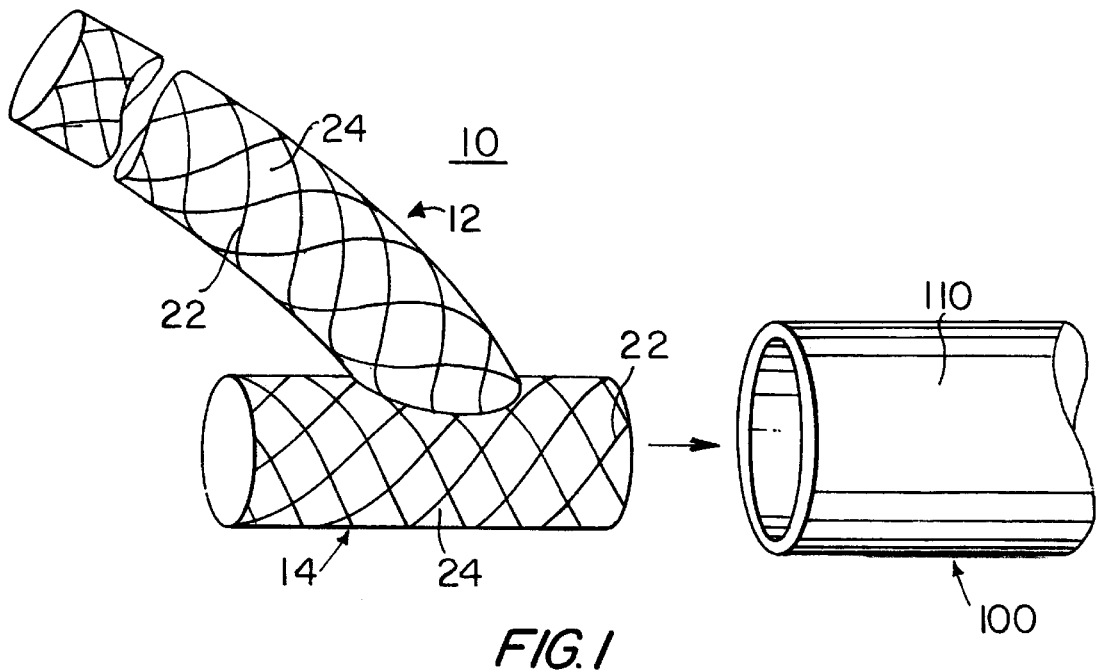
FIG. 1 is a simplified elevational view of an illustrative embodiment of a tubular graft connector and part of illustrative apparatus for installing a tubular graft connector, all in accordance with this invention.

An illustrative embodiment of a tubular graft connector 10 in accordance with this invention for connecting the end of a tubular graft to an aperture in the side wall of a patient's tubular body tissue structure is shown in FIG. 1. Connector 10 includes a tubular first section 12 tubularly connected to a tubular second section 14. The longitudinal axis of second section 14 extends transversely to the longitudinal axis of first section 12. It will be understood that "transverse" can mean perpendicular, but it can also mean acute or obtuse angles other than 90°. In the particular embodiment shown in FIG. 1, second section 14 extends in both directions from the adjacent end of first section 12 so that connector 10 has the approximate shape of a capital letter T. The lumens through first and second sections 12 and 14 communicate with one another inside the connector where the two sections meet.

In the particular embodiment shown in FIG. 1 connector 10 includes an open mesh framework 22 (e.g., a braid of nitinol, stainless steel, or tungsten wires or polymer strands) which may be covered with a rubber-like web 24 (e.g., of silicone). Thus connector 10 may be constructed like various artificial grafts shown and described in the above-mentioned Goldsteen et al. reference. Indeed, many of the graft variations described in the Goldsteen et al. reference are equally suitable for connector 10. Also in the particular embodiment shown in FIG. 1, first section 12 is of sufficient length that it actually forms an artificial graft structure. In other words, in this case first section 12 is integral with an artificial graft structure. Alternatively, section 12 could be made shorter for tubular attachment to an initially separate artificial or natural graft. In general, references herein to attachment of a connector to a graft structure will be understood to be generic to both (1) integral formation of the connector and graft structure, and (2) initially separate formation and subsequent joining of the connector and graft structure. If section 12 is initially separate from the graft structure, it may be attached to the graft structure by inserting it coaxially in an end portion of the graft structure. Section 12 may then resiliently expand to annularly engage the end portion of the graft structure. In addition, section 12 may be sutured to the graft structure. Or section 12 may have radially outwardly projecting prongs (which may be hooked and/or barbed) to improve engagement and retention of the graft structure by section 12. As still another possibility, section 12 may be crimped around the outside of an axial end portion of the graft conduit as is described in more detail in connection with several later embodiments. Adhesive may also be used in connections between the connectors of this invention and the associated tubular conduits. Additional information regarding various ones of these alternatives is provided in connection with other embodiments that are discussed below. In many cases the connector and graft conduit can be connected to one another in advance and outside the patient's body. This eliminates space constraints for suturing inside the body, and in the coronary area it also eliminates the complexity of suturing to a beating heart.

First and second sections 12 and 14 may be joined to one another in any of a variety of ways. For example, these two sections may be sutured together, welded together, or formed integrally. Particularly preferred joining techniques are shown in later FIGS. and described below.

An advantageous characteristic of the above-described connector structures (e.g., a nitinol framework covered by a silicone web) is that they are extremely elastic and resilient. Thus they can be radically deformed (e.g., during installation), and they thereafter return to their original shape without any damage or memory that they were deformed. This type of structure is also flexible in use so that it may advantageously pulse in response to blood pressure pulses when it is used in a patient's circulatory system. In other words, the connector is compliant under blood pressure.

Figure 2:
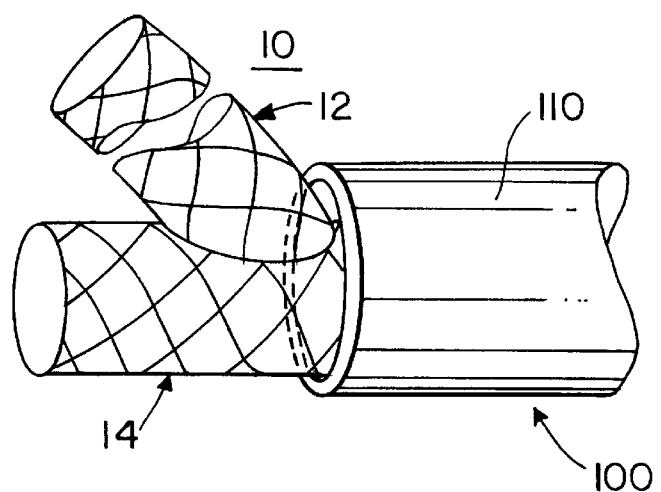
FIG. 2 is a view similar to FIG. 1 showing a later stage in use of the FIG. 1 connector and apparatus in accordance with the invention.
Figure 3:
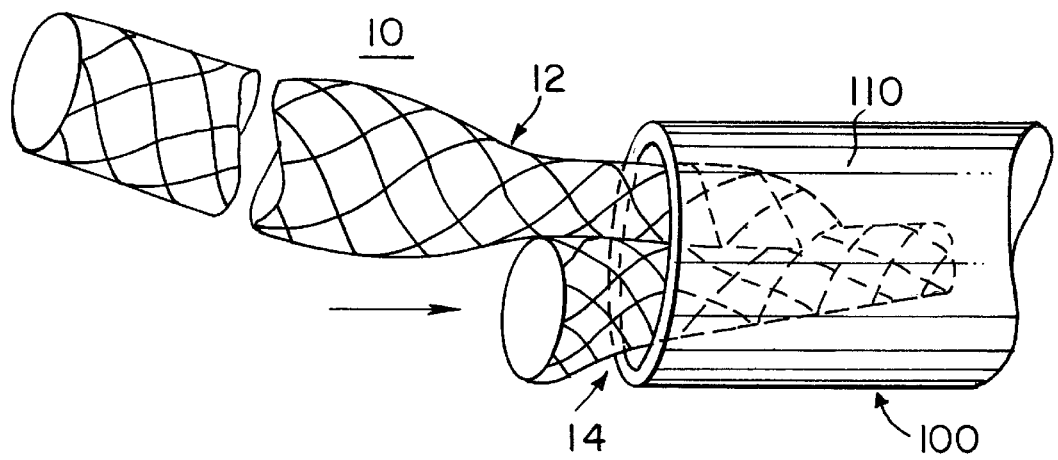
FIG. 3 is another view similar to FIG. 2 showing a still later stage in use of the FIG. 1 connector and apparatus in accordance with the invention.
Figure 4:
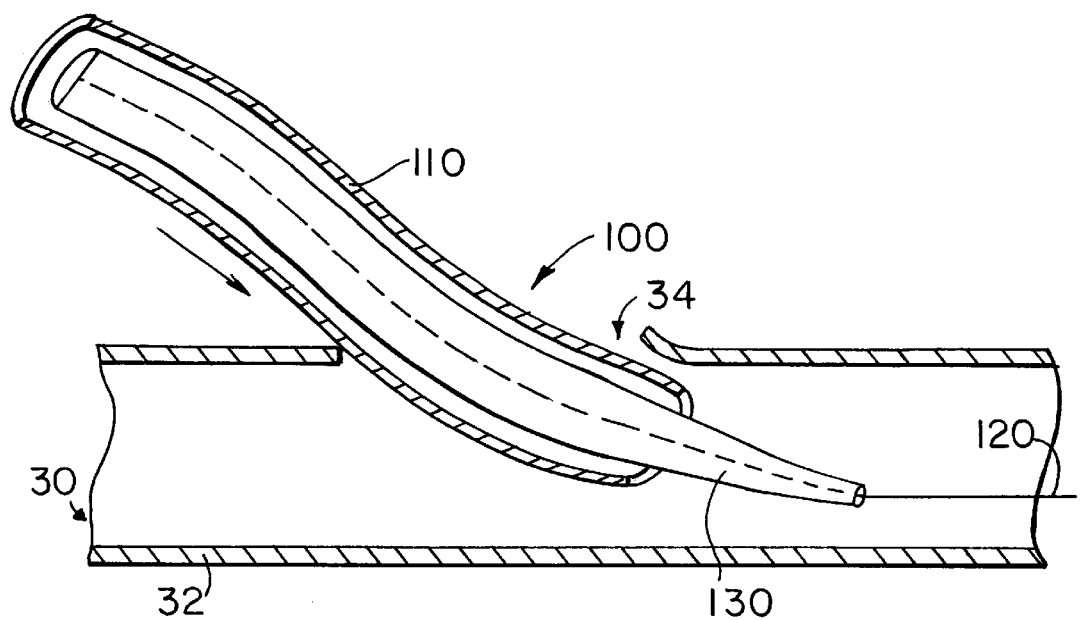
FIG. 4 is a simplified view, partly in section, of another stage in use of the FIG. 1 connector and apparatus in accordance with the invention.

In addition to showing illustrative connector 10, FIG. 1 shows part of illustrative apparatus 100 for installing a connector like connector 10 in a patient. The portion of apparatus 100 that is shown in FIG. 1 comprises delivery tube or sleeve 110. FIGS. 2 and 3 show progressive insertion of connector 10 into sleeve 110. In particular, one end portion of second section 14 is inserted into sleeve 110 as shown in FIG. 2. Then first section 12 is folded down along the other end portion of second section 14 so that the remainder of connector 10 can be pushed into sleeve 110 as shown in FIG. 3.

Figure 5:
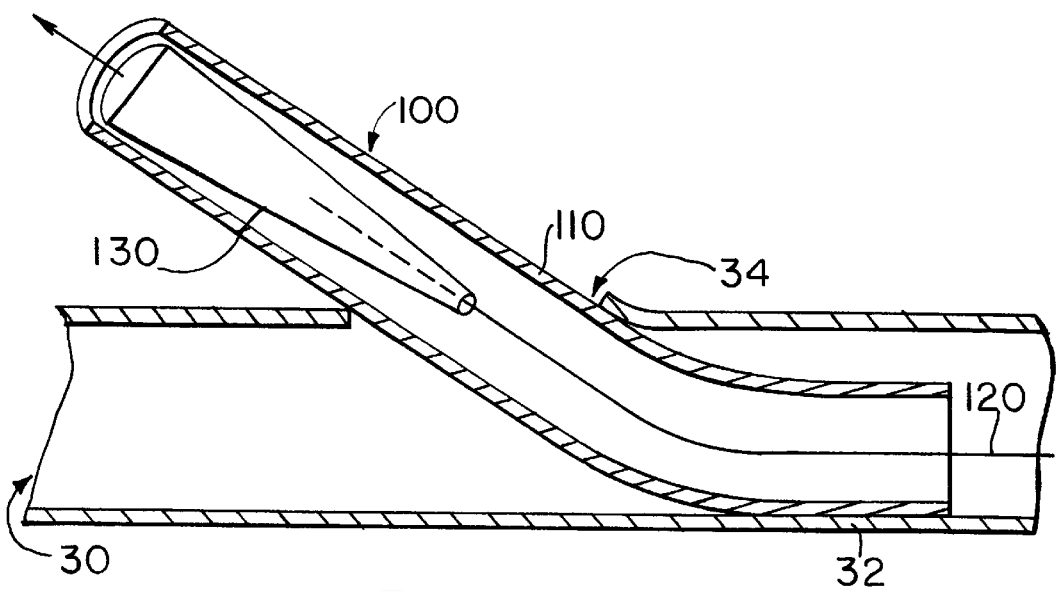
FIG. 5 is a view similar to FIG. 4 showing a later stage in use of the connector and apparatus in accordance with the invention.

Additional details regarding illustrative construction and use of apparatus 100 are shown in FIGS. 4–8. These FIGS. show apparatus 100 being used to install connector 10 through an aperture 34 in the side wall 32 of a patient's tubular body tissue structure 30 (e.g., a blood vessel). In particular, longitudinal guide structure 120 (e.g., a wire) is first inserted through aperture 34 into the lumen of body structure 30. Then a dilator structure 130 is advanced along and concentrically around guide structure 120 so that its distal, conically tapered, nose portion opens up aperture 34. The next step is to advance the distal portion of sleeve 110 over dilator 130, through dilated aperture 34, and into the lumen of body conduit 30 as shown progressively in FIGS. 4 and 5. Dilator structure 130 may then be withdrawn proximally as is also shown in FIG. 5 and ultimately removed from sleeve 110.

Figure 6:
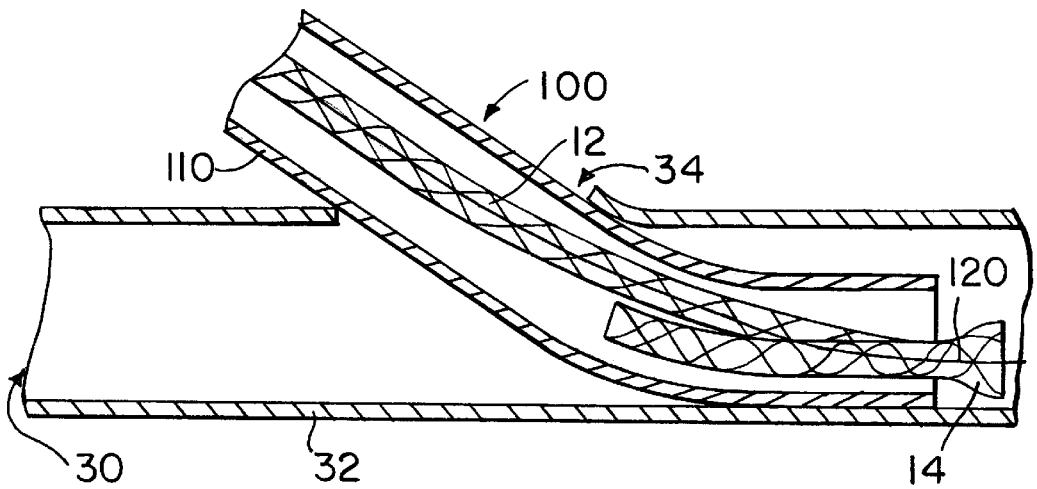
FIG. 6 is another view similar to FIG. 5 showing a still later stage in use of the connector and apparatus in accordance with the invention.

A subsequent step is shown in FIG. 6 and involves inserting connector 10 into and along sleeve 110 so that portions of connector 10 are disposed around guide structure 120. In particular, connector 10 may be initially inserted into the proximal end of sleeve 110 as shown in FIGS. 1–3, but with the addition of guide structure 120 passing through first section 12 and the end portion of section 14 that first section 12 is not folded back along.

Figure 7:
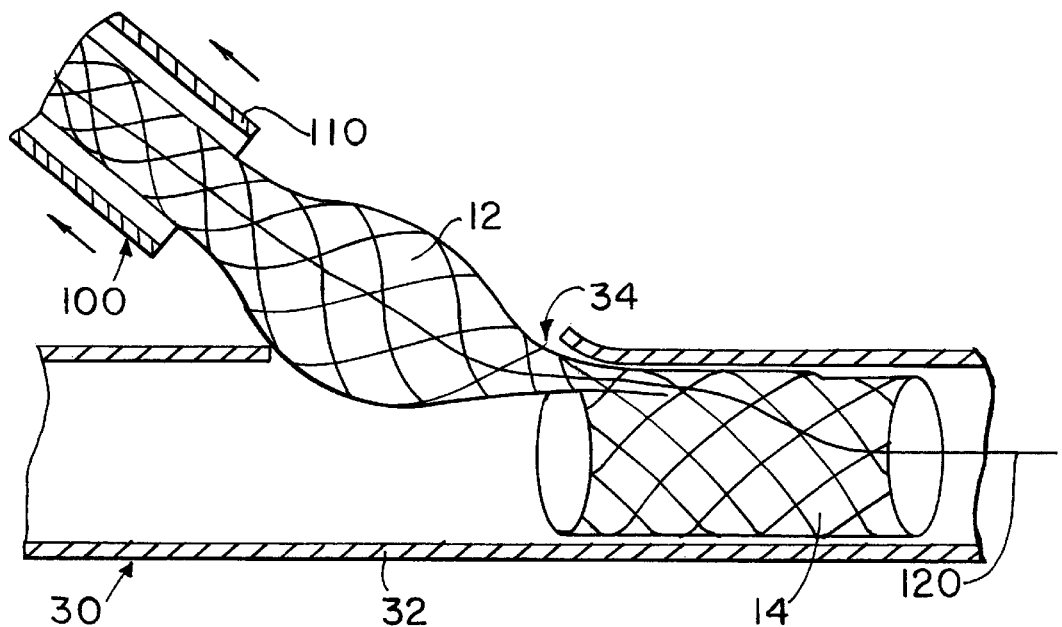
FIG. 7 is still another view similar to FIG. 6 showing yet a later stage in use of the connector and apparatus in accordance with the invention.
Figure 8:
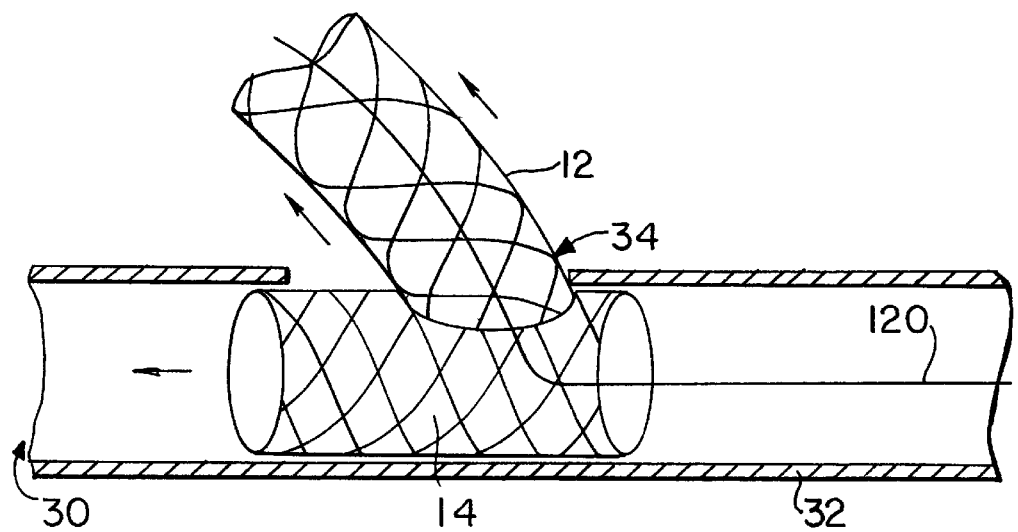
FIG. 8 is yet another view similar to FIG. 7 showing a still later stage in use of the connector and apparatus in accordance with the invention.
Figure 9:
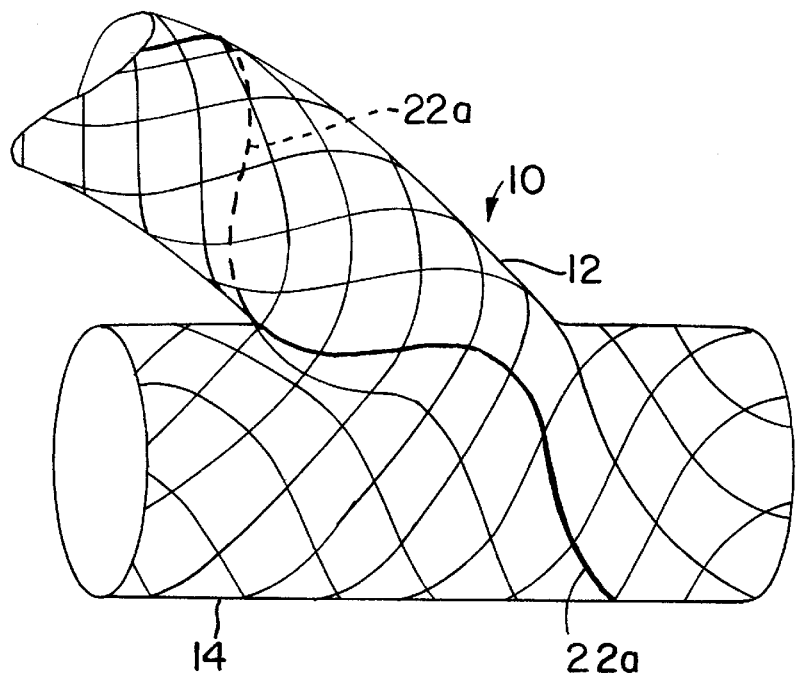
FIG. 9 is a simplified elevational view showing in more detail a possible construction of a connector of the type shown in FIG. 1.

When connector 10 has been pushed far enough along sleeve 110 so that all of second section 14 is inside the lumen of body conduit 30 as shown in FIG. 6, sleeve 110 can be pulled proximally as shown in FIG. 7. This leaves second section 14 disposed concentrically inside the lumen of conduit 30, with first section 12 extending part way out of aperture 34. Then, as shown in FIG. 8, first section 12 can be pulled back in the direction from which the connector was inserted. This shifts second section 14 along the lumen of conduit 30 until first section 12 is centered on aperture 34 and therefore extends out of the aperture with no remaining folding of the first section along second section 14. Connector 10 is now fully installed in conduit 30 and elements 110 and 120 can be removed if or when not needed for any further steps. Second section 14 resiliently expands when released from sleeve 110 to approximately the same size as the interior of body conduit 30. Thus second section 14 resiliently and annularly bears on the inner surface of the side wall 32 of conduit 30. This helps to secure connector 10 in conduit 30.

Figure 10:
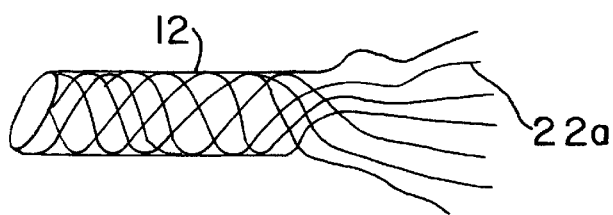
FIG. 10 is a simplified elevational view of a portion of the FIG. 9 apparatus at a predetermined point in its fabrication.
Figure 11:
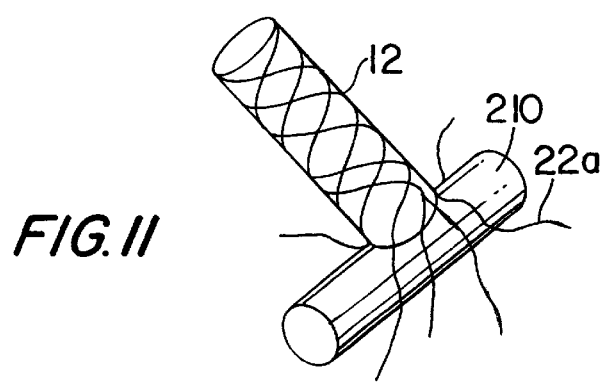
FIG. 11 is a view similar to FIG. 10 showing a later stage in the fabrication process.

Illustrative, especially preferred, techniques for producing connectors 10 of the type shown in the previously described FIGS. are shown in FIGS. 9–12. In the embodiment shown in FIGS. 9–11 mesh framework strands 22 (one representative strand 22a being emphasized in FIG. 9 for purposes of illustration) that extend from an end of first section 12 as shown in FIG. 10 are woven or braided around cylindrical mandrel 210 as shown in FIG. 11 to produce the T-shaped finished connector framework shown in FIG. 9. In other words, first section 12 is formed first as shown in FIG. 10 with unbraided strands 22 of the connector framework left extending from one end of that first section. Then these initially unbraided strands are used to weave or braid second section 14 around mandrel 210 as shown in FIG. 11. Thus in the finished connector framework shown in FIG. 9 framework strands 22 are unbroken and continuous between first and second sections 12 and 14 (as is apparent from considering representative strand 22a in FIG. 9).

Figure 12:
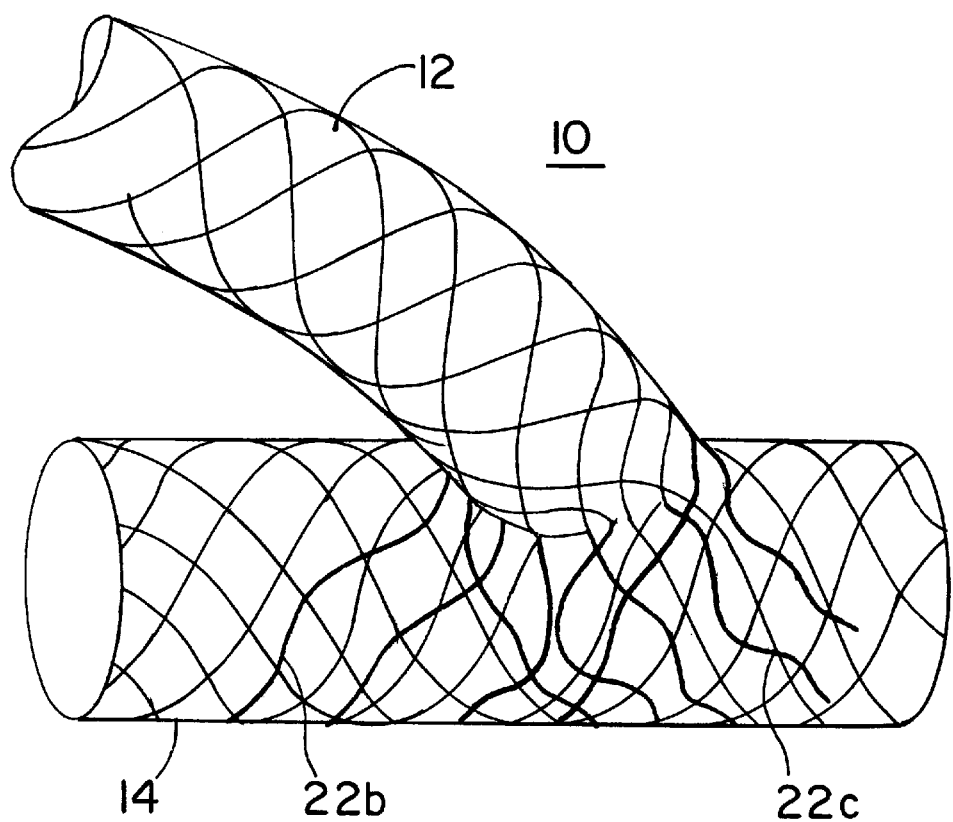
FIG. 12 is a simplified elevational view showing in more detail another possible construction of a connector of the type shown in FIG. 1.

In the alternative embodiment shown in FIG. 12 framework strands (e.g., emphasized strands 22b and 22c) that initially extend unbraided from an end of first section 12 are woven into the framework of second section 14. In other words, second section 14 is formed using framework strands 22 that are separate from the framework strands 22 that are used to form first section 12. However, the unbraided extensions of the first section strands are woven into the second section framework to unite the two sections as shown in FIG. 12.

Figure 13:
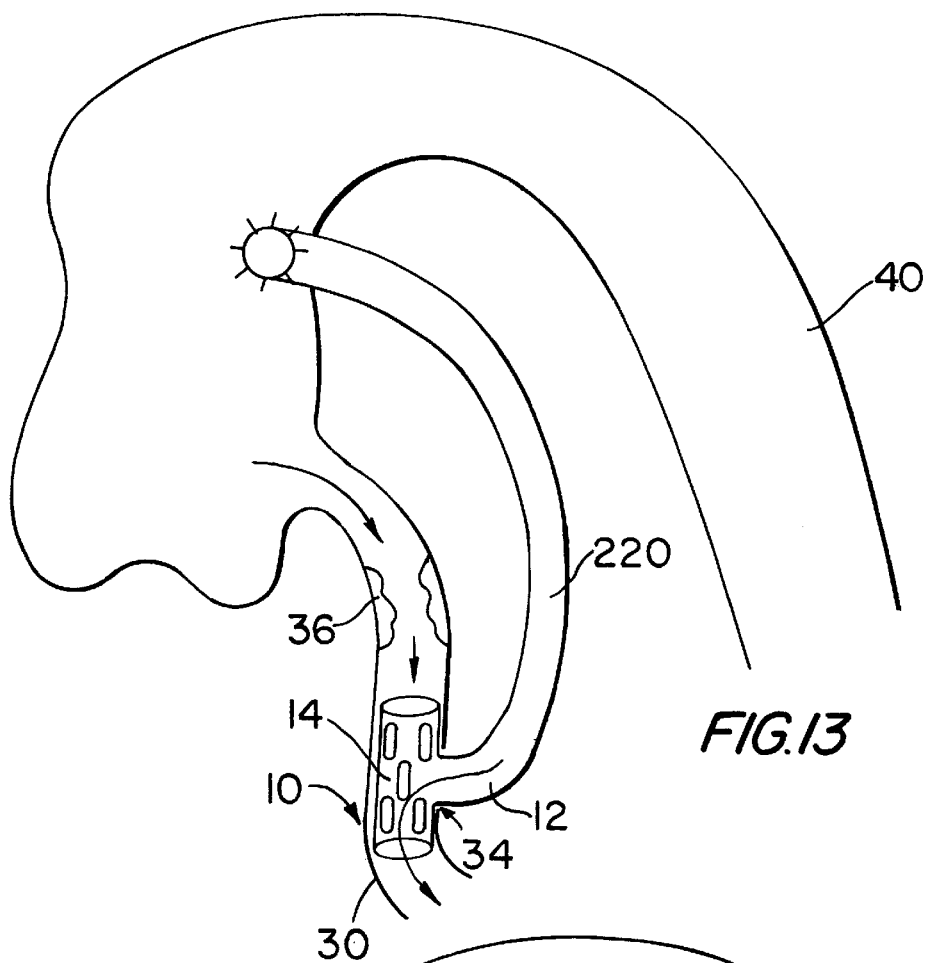
FIG. 13 is a simplified elevational view, partly in section, showing an illustrative use of a connector of this invention in a patient.

FIG. 13 shows just one example of possible use of connectors of the type shown in the previously described FIGS. In this example, connector 10 is used to connect one end of a coronary bypass graft 220 to the coronary artery 30 of a patient downstream from a partial occlusion 36 of that artery. The other end of graft 220 is connected to an aperture in the side wall of the patient's aorta 40 (see FIGS. 36–39 and the discussion of those FIGS. below for an example of a connector that can be used to connect graft conduit 220 to an aperture in the side wall of much larger aorta 40). Second section 14 of connector 10 is disposed concentrically inside artery 30. First section 12 of connector 10 extends out of an aperture in the side wall of artery 30 and is connected to or integral with graft 220. Accordingly, graft 220 and connector 10 cooperate to allow blood to flow from aorta 40 to artery 30 downstream from partial occlusion 36. This blood flow supplements the flow of blood through occlusion 36, thereby relieving the patient of the adverse effects of occlusion 36.

Figure 14:
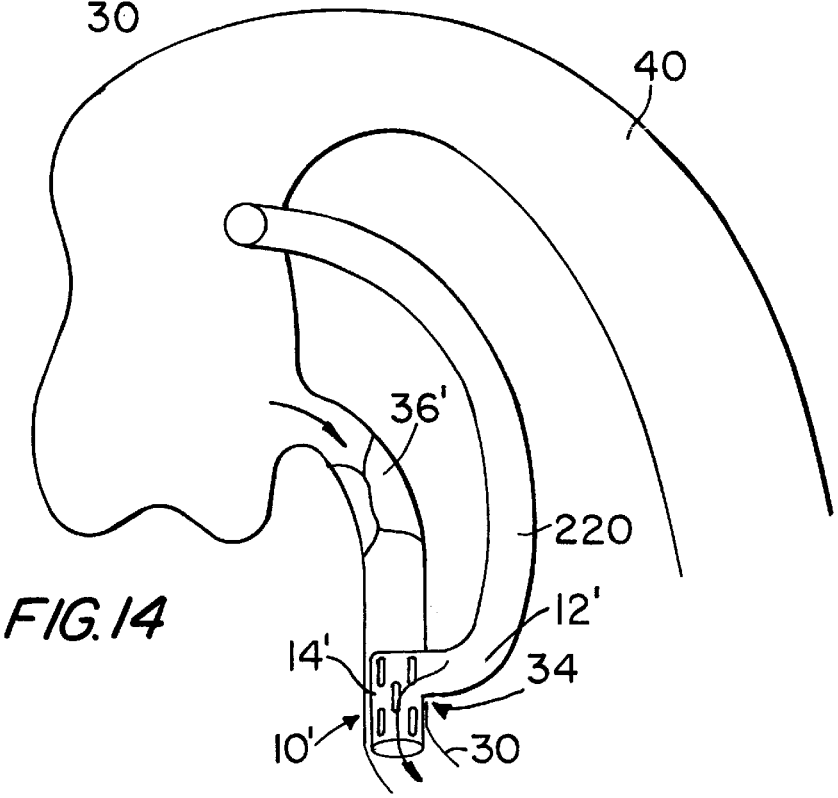
FIG. 14 is another view similar to FIG. 13 showing an illustrative use of an alternative connector in accordance with this invention.

It may not be necessary in all cases for the connectors of this invention to have a full T shape. For example, FIG. 14 shows an illustrative use of a connector 10' in accordance with this invention in a bypass around a total occlusion 36' in a patient's coronary artery 30. Instead of being T-shaped, connector 10' is more nearly L-shaped. In other words, second section 14' of connector 10' extends transversely in only one direction from the adjacent end of first section 12'. In particular, second section 14' extends from first section 12' in the downstream direction in coronary artery 30. The upstream end of second section 14' can be closed or substantially closed because no blood is coming from that direction due to the presence of total occlusion 36'. In other respects the structures shown in FIG. 14 can be similar to what is shown in FIG. 13. If desired, connector 10' can be inserted in artery 30 (or any other tubular body conduit) in substantially the same way that connector 10 is inserted (e.g., using apparatus of the type shown in FIGS. 1–8). The only difference is that in the case of connector 10', second section 14' extends in only one direction along conduit 30 from aperture 34.

Figure 14A:
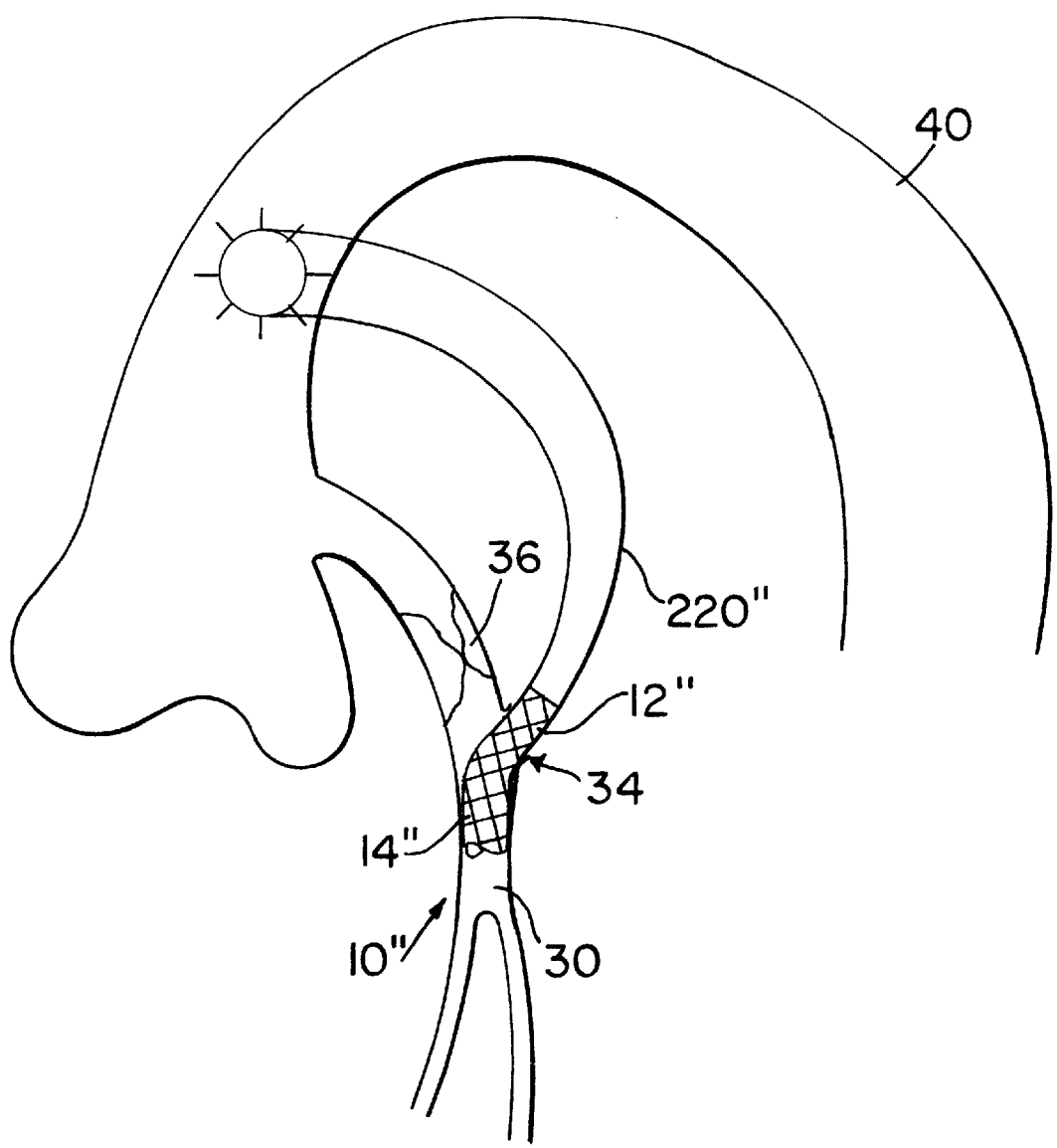
FIG. 14a is yet another view similar to FIGS. 13 and 14 showing another illustrative embodiment of the invention.

FIG. 14a shows an alternative installation of an L-shaped connector 10". As in earlier embodiments, connector 10" can be initially separate from or integral with graft vessel 220". For example, the design may utilize shape memory braid over a tapered and formed mandrel, and may be shaped to match the inner lumen size of the grafted vessel and tapered to transition from the aortic connection to the inner lumen dimension.

As will be appreciated from the foregoing, the connectors and connector insertion apparatus of this invention are suitable for use in conventional surgery and in less invasive patient treatment procedures such as percutaneous laparoscopy and intraluminal procedures of the kind described in the first three references mentioned above. If the target body conduit 30 has been exposed surgically, apparatus 100 can be made to approach the body conduit through the surgical opening. With regard to laparoscopic or intraluminal procedures, the connectors of this invention have (or can be folded to have) relatively small cross sections. Apparatus 100 can also have a small cross section. This allows the connector and associated apparatus 100 to be inserted into the patient via the relatively small passageways or instruments that are used for laparoscopy. Similarly, such small cross sections allow the connector and associated apparatus 100 to be inserted into the patient intraluminally.

Figure 15:
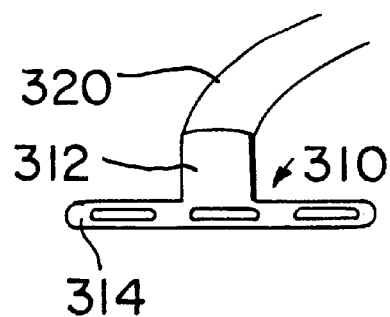
FIG. 15 is a simplified elevational view, partly in section, of another illustrative embodiment of a graft connector in accordance with this invention.
Figure 16:
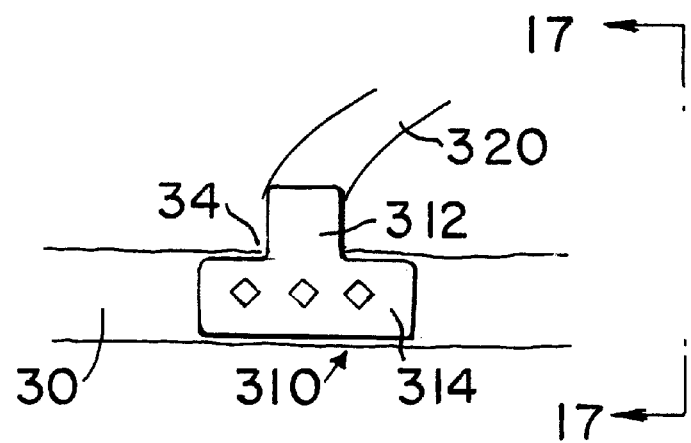
FIG. 16 is another view similar to FIG. 15 showing a later stage in use of the connector of FIG. 15.
Figure 17:
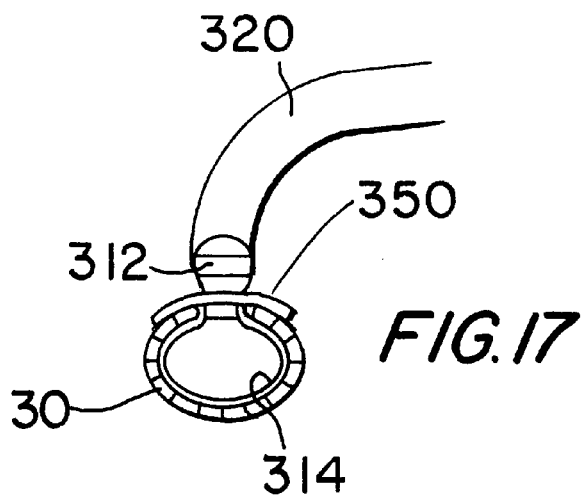
FIG. 17 is a view taken generally along the line 17—17 in FIG. 16, but with additional structure in accordance with this invention added.

FIG. 15 shows another illustrative T-shaped connector 310 in accordance with the invention. Connector 310 includes a first section 312 which is adapted to be received in an end of a tubular graft 320. Connector 310 also includes a second section 314 which initially has a relatively small cross section as shown in FIG. 15, but which is circumferentially enlargeable to a relatively large cross section as shown in FIGS. 16 and 17. For example, second section 314 may be a modified (e.g., perforated) metal tube which is circumferentially expandable by a selectively inflatable balloon inside that section. Connector 310 is typically inserted into a patient's tubular body conduit 30 with second section 314 in its relatively small cross-sectional configuration. Then second section 314 is circumferentially expanded so that it annularly engages the inner surface of the side wall 32 of the conduit 30. Graft conduit 320 (which, as in other embodiments, may be artificial conduit, natural conduit, or a combination of both) may be attached to first section 312 before or after second section 314 is inserted in conduit 30. An annular external seal 350 (FIG. 17) can be applied over the connector around aperture 34 to provide a hemodynamic seal and to promote in-growth of tissue to further reinforce vessel connection over time. Examples of materials suitable for use in making seal 350 are silicone and urethane.

Another illustrative T-shaped connector 410 is shown in FIG. 18. Connector 410 includes a first section 412 that may be a tubular framework. Connector 410 also includes a second section 414 that comprises spring coils that extend transversely from an end portion of first section 412. Sections 412 and 414 may made of shape memory materials similar to those mentioned above for the framework of sections 12 and 14 in FIG. 1. Second section 414 is axially compressible as shown in FIG. 19 to facilitate insertion of the second section through an aperture 34 in a side wall of a patient's tubular body conduit 30. After second section 414 has been inserted through aperture 34 in the axially compressed condition shown in FIG. 19, the axial compression of the second section is released so that the second section can spring back to its original condition but inside the lumen of conduit 30 as shown in FIG. 20. Graft conduit 420 may be artificial, natural, or both, and may be attached to first section 412 (e.g., by suturing) at any convenient time either before or after insertion of second section 414 in conduit 30. First section 412 may be inserted into an axial end portion of graft conduit 420 and allowed to resiliently expand into annular engagement with that end portion. Or first section 412 may be crimped around the outside of the end portion of graft conduit 420. Protrusions from first section 412 may penetrate the end portion of conduit 420 to more securely attach these two structures. These protrusions may be hooked and or barbed for even better retention of conduit 420. Some of these alternatives are discussed in more detail in connection with subsequently described embodiments. If desired, an annular seal 450 (similar to above-described seal 350) may be placed around the outside of the joint between graft 420 and conduit 30 as shown in FIGS. 21 and 22 for purposes similar to those described above for seal 350. Although all of the connectors of this invention facilitate and thereby speed up the making of graft connections, embodiments like the one shown in FIGS. 18–22 are particularly quick to install. Embodiments of this kind therefore have especially "quick-connect" characteristics.

Figure 23:
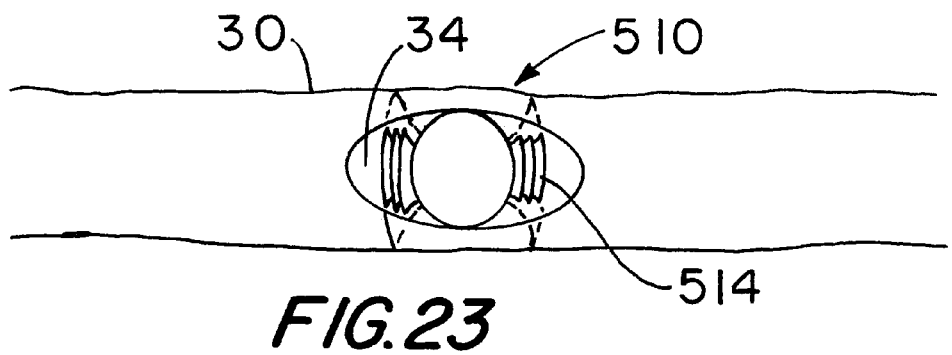
FIG. 23 is a simplified elevational view of still another illustrative graft connector in accordance with the invention.
Figure 24:
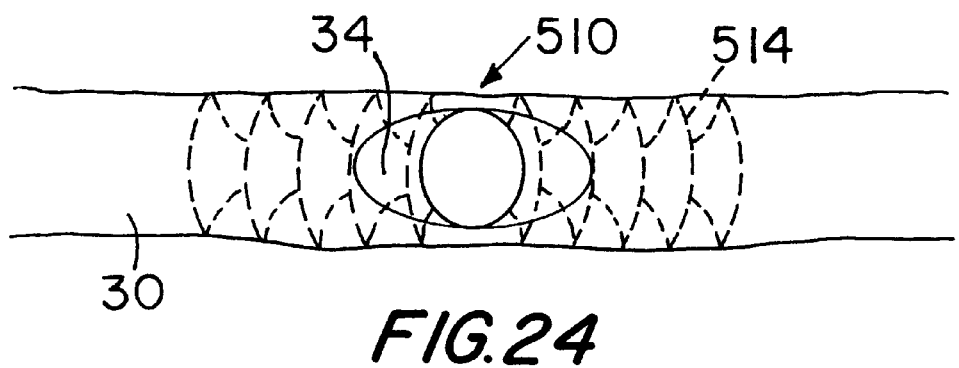
FIG. 24 is another view similar to FIG. 23 showing another operating condition of the FIG. 23 connector.
Figure 25:
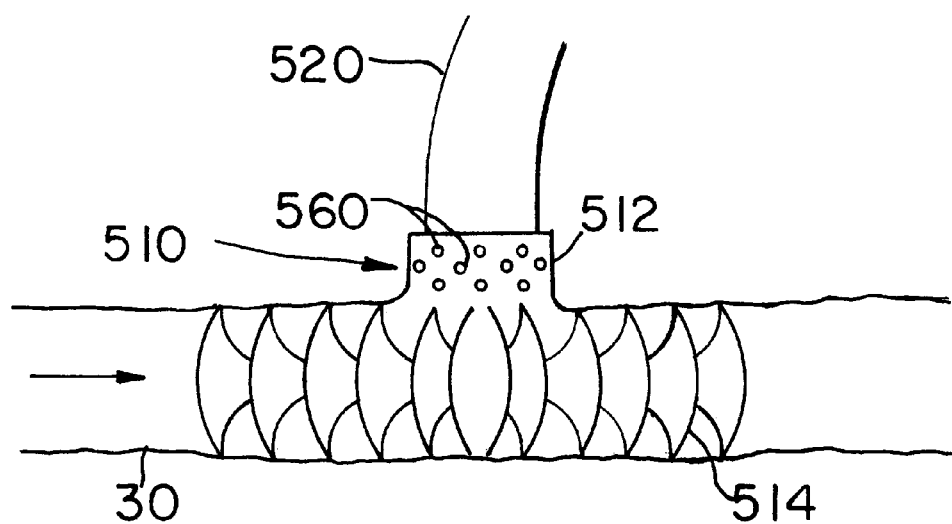
FIG. 25 is a simplified elevational view, partly in section, taken perpendicular to the view shown in FIG. 24.

Rather than being just a single spring coil as shown in FIGS. 18–22, more complex spring shapes can be used for second section 414, one example being shown at 514 in FIGS. 23–25. Illustrative constructions of section 514 include a resilient, axially compressible spring braid or a self-expanding nitinol tube. The second section is axially compressed as shown in FIG. 23 to facilitate insertion of the second section through aperture 34 in the side wall of body conduit 30. After second section 514 is through aperture 34, the axial compression of the second section is released so that it springs out along the lumen of conduit 30 as shown in FIGS. 24 and 25. Section 514 may have a rubber-like (e.g., silicone) outer cover to prevent leakage via aperture 34 around first section 512.

FIG. 25 illustrates another possible constructional feature of the connectors of this invention. This is a circumferentially crimpable first section 512 (e.g., of nitinol or stainless steel). In particular, crimpable first section 512 has an initially relatively large circumference into which an end of tubular graft 520 can be inserted. First section 512 is then circumferentially crimped to reduce its circumference and cause it to annularly engage the outside of graft conduit 520. The inner surface of first section 512 may have radially inwardly extending prongs 560 (e.g., of nitinol or stainless steel) to penetrate or at least deform the material of graft conduit 520 and thereby help to retain the graft conduit in the first section. Prongs 560 may be hooked (i.e., curved) and/or barbed (somewhat like fishhooks) to still further strengthen the connection between graft conduit 520 and connector 510. Adhesive may also be used to further secure the connector to graft conduit 520. It may be advantageous to secure the connector to the outside of the graft conduit in this general way because it reduces possible obstruction of fluid flow in the graft conduit due to the presence of the connector. In the case of natural graft conduits, securing the connector to the outside of that conduit helps protect the delicate internal lumen of the conduit.

Figure 27:
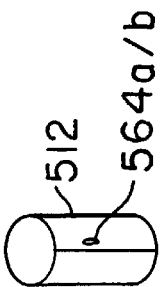
FIG. 27 is a view similar to FIG. 26 showing another operating condition of the FIG. 26 apparatus.
Figure 26:
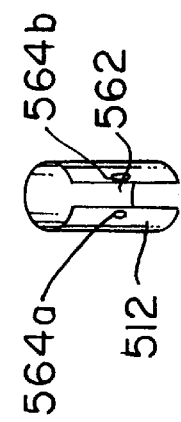
FIG. 26 is a simplified perspective view of an illustrative embodiment of a portion of a connector in accordance with the invention.
Figure 28:
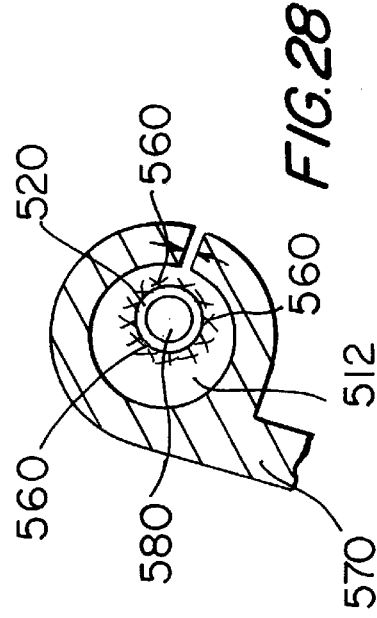
FIG. 28 is a simplified sectional view of an illustrative embodiment of a portion of a connector in accordance with the invention and instrumentation usable in applying the connector.
Figure 39:
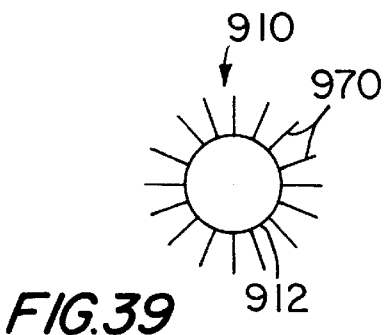
FIG. 39 is a simplified end view of the connector shown in FIG. 36.

FIG. 26 shows that crimpable first section 512 may initially have an axially extending gap 562 in its side wall. After graft conduit 520 has been inserted in first section 512, gap 562 is closed (e.g., by use of a crimping tool 570 as shown in FIG. 28). Closing gap 562 allows latching elements 564a and 564b on respective opposite sides of the gap to interengage and latch as shown in FIG. 27, thereby holding the gap closed. A mandrel 580 may be placed inside graft conduit 520 during operation of crimping tool 570 to ensure that first section 512 and its prongs 560 (if any) properly engage the graft conduit. As an alternative to crimping by closing a gap, a crimpable connector section may be made of a crimpable material or some other crimpable structure. For example, a split and overlapping ring structure may be used as shown in FIG. 39 and described in more detail below.

Figure 29:
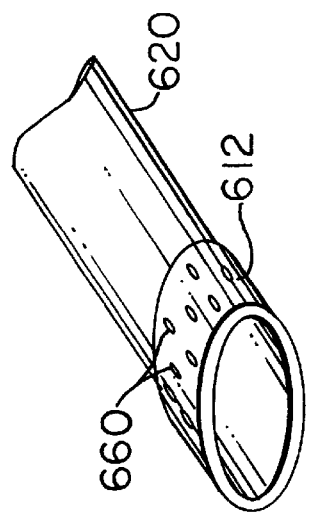
FIG. 29 is a simplified perspective view of another illustrative embodiment of a portion of a connector in accordance with the invention.

It should be mentioned that various sections of the connectors of this invention do not have to be circular in cross section. For example, the first section of a connector can have an oval cross section if desired. This may be useful, for example, when it is necessary to connect an end of a relatively large graft conduit to the side wall of a somewhat smaller conduit 30. FIG. 29 shows an example of an oval crimp-type connector or connector portion 612. As in the embodiments illustrated by FIGS. 25–28, connector portion 612 is crimped around the outside of graft conduit 620 and has radially inwardly extending prongs 660 for penetrating the material of the graft conduit to more securely engage that conduit.

Figure 30:
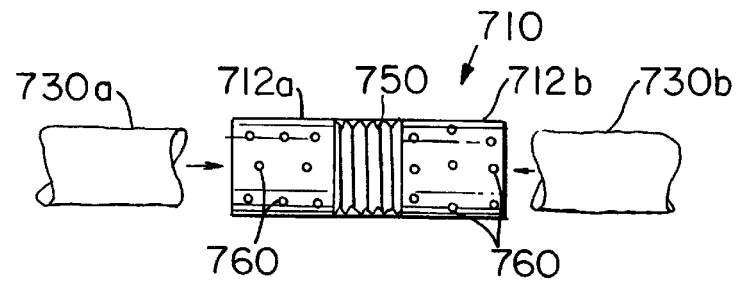
FIG. 30 is a simplified elevational view of an illustrative embodiment of a somewhat different type of connector in accordance with the invention.
Figure 31:
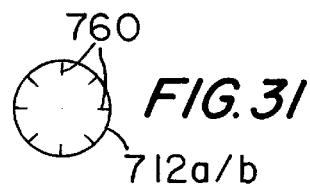
FIG. 31 is a simplified end view of the connector shown in FIG. 30.
Figure 32:
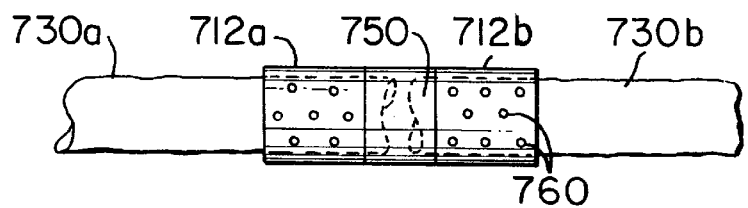
FIG. 32 is a view similar to FIG. 30 showing a later stage in use of the FIG. 30 connector.

FIGS. 30–32 show application of certain of the principles of this invention to end-to-end connectors. In particular, connector 710 is to be used to connect an end of vessel 730a to an end of vessel 730b. For example, one of these vessels may be a tubular graft conduit. Connector 710 includes two axially aligned tubular end sections 712a and 712b joined by an intermediate tubular seal section 750. Each of end sections 712 is circumferentially crimpable to annularly engage the outer surface of the end of a respective one of vessels 730 which has been inserted in that end section (see FIG. 32). Prongs 760 extend radially inwardly from each of end sections 712 as shown in FIG. 31 to better hold the associated vessel in that end section. Seal section 750 (e.g., of silicone or urethane) prevents leakage from the ends of the vessels 730 that have been joined by the connector.

Figure 33:
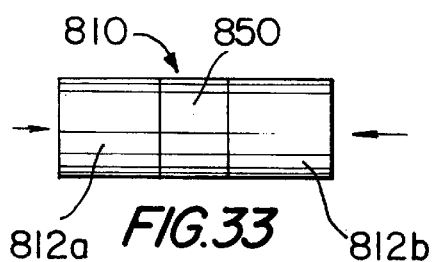
FIG. 33 is another view similar to FIG. 30 showing another illustrative embodiment of a connector of the general type shown in FIG. 30.
Figure 34:
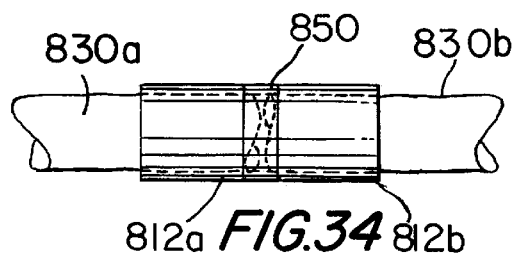
FIG. 34 is another view similar to FIG. 33 showing a later stage in use of the FIG. 33 connector.
Figure 35:
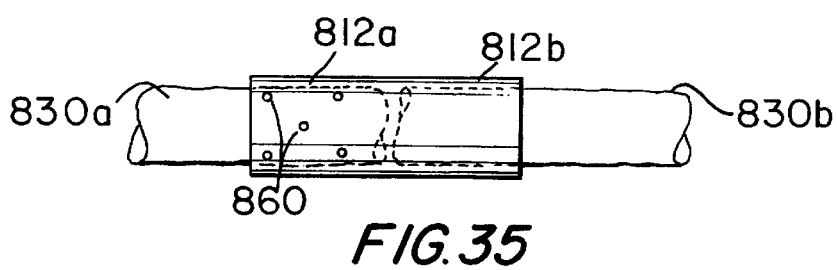
FIG. 35 is another view similar to FIG. 34 showing a still later stage in use of the FIG. 33 connector.

An alternative embodiment of an end-to-end connector 810 is shown in FIGS. 33–35. Connector 810 is similar to connector 710, except that seal section 850 (again, e.g., of silicone or urethane) is axially compressible. Thus after the ends of vessels 830a and 830b are inserted into connector sections 812a and 812b, and those connector sections are crimped around the vessel ends, sections 812a and 812b are forced toward one another to axially compress seal section 850. This helps bring the ends of vessels 830a and 830b together inside the connector. If vessels 830a and 830b are both natural tissue, bringing their ends together helps to promote healing between the vessel ends.

Another illustrative application of the crimpable connector technology of this invention is shown in FIGS. 36–39.

Figure 36:
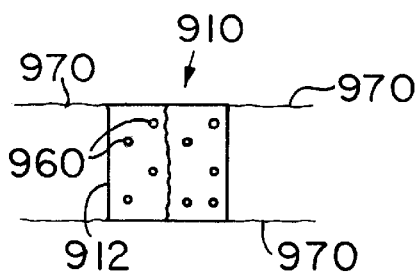
FIG. 36 is a simplified elevational view of an illustrative embodiment of still another somewhat different type of connector in accordance with the invention.

Connector 910 is shown by itself prior to crimping and installation in FIG. 36. Connector 910 includes crimpable tubular section 912 which has resilient struts 970 (e.g., of nitinol wire) that extend radially out from both of its axial ends. Connector 910 illustrates an alternative crimpable structure in which section 912 is an axially slit tube with the slit edge portions radially overlapping one another (see also FIG. 39). This structure is crimped to reduce its initially relatively large circumference by increasing the amount of overlap of the slit edge portions. This principle is applicable to any of the crimpable connector structures shown and described herein.

Figure 37:
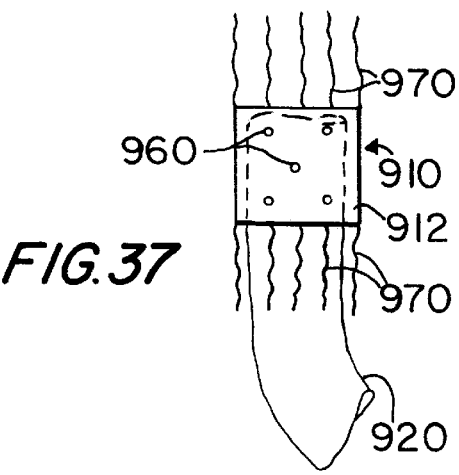
FIG. 37 is another view similar to FIG. 36 showing a later stage in use of the connector shown in FIG. 36.
Figure 38:
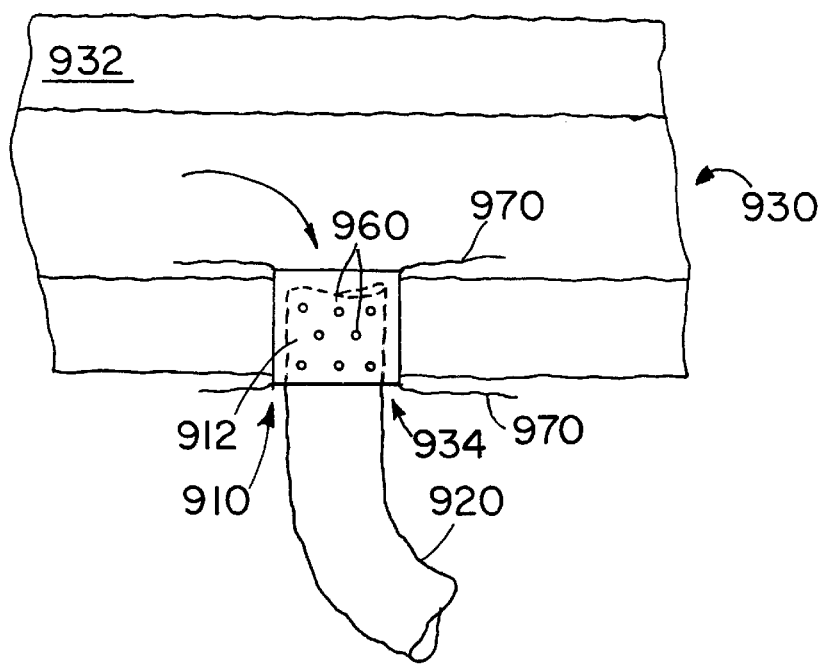
FIG. 38 is another view similar to FIG. 37 showing a still later stage in use of the connector shown in FIG. 36.

To use connector 910 the end portion of a conduit 920 to be connected to an aperture 934 in the side wall 932 of another conduit 930 is inserted in section 912 and section 912 is crimped around that end portion of conduit 920 as shown in FIG. 37. For example, conduit 920 may be a graft conduit which is to be connected to a patient's body conduit 930. Prongs 960 extend into the side wall of conduit 920 as in related previously described embodiments. Struts 970 are deflected substantially parallel to the longitudinal axis of conduit 920. This may be done, for example, by surrounding the structure shown in FIG. 37 with a delivery tube (not shown). In the condition shown in FIG. 37 connector 910 is installed in aperture 934 and struts 970 are released so that they can resiliently spring out and resume their initial positions as shown in FIGS. 38 and 39. By extending radially out from section 912, struts 970 bear on both the inner and outer surfaces of conduit side wall 932. Struts 970 thereby hold connector 910 and conduit 920 in the position required to connect conduit 920 to conduit 930. Connectors of the type shown in FIGS. 36–39 are particularly suitable for connecting an end of a relatively small conduit 920 to the side wall of a relatively large conduit 930. For example, a connector of this type can be used in FIGS. 13–14a to connect the upstream end of graft conduit 220 or 220" to aorta 40.

Figure 41:
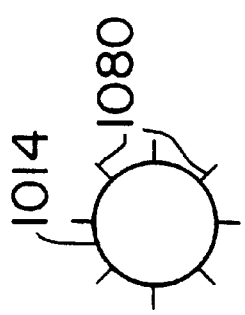
FIG. 41 is a simplified end view of the connector shown in FIG. 40.
Figure 40:
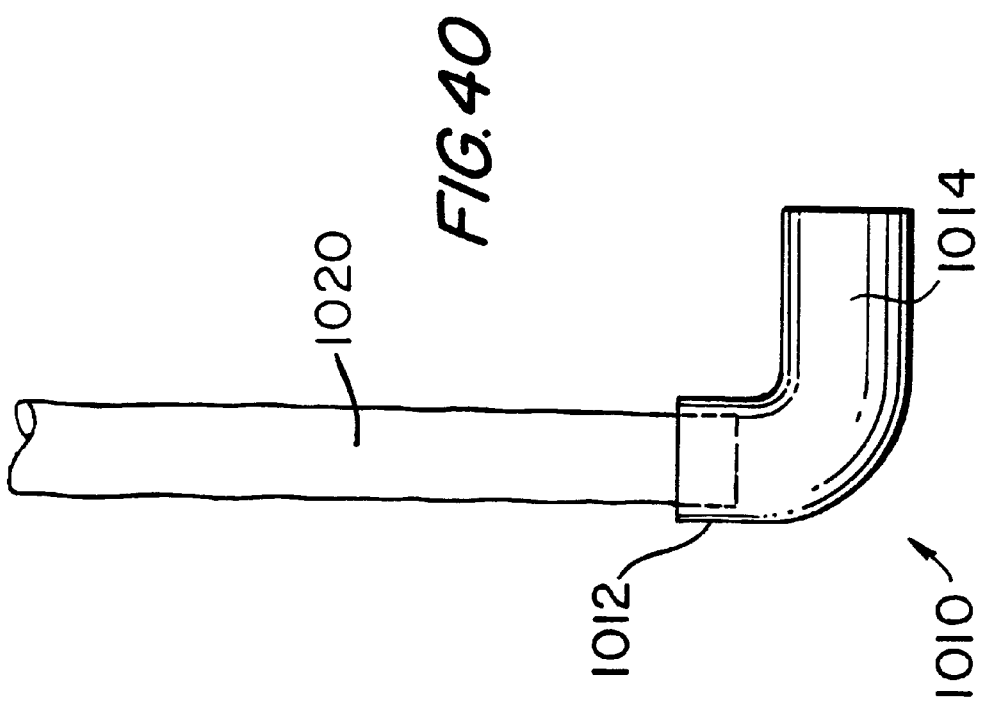
FIG. 40 is a simplified elevational view of another illustrative embodiment of a connector in accordance with the invention.

FIGS. 40 and 41 show another illustrative embodiment of an L-shaped connector 1010 in accordance with this invention. Connector 1010 may be braided or coiled strands of nitinol, stainless steel, tungsten, or polymer, or nitinol tubing, as in other previously described embodiments. Connector 1010 includes a first section 1012 which may be crimpable around an end portion of tubular conduit 1020 as in related previously described embodiments. Alternatively or in addition, first section 1012 may include hooks and/or barbs for connection to conduit 1020. Second section 1014 extends transversely from first section 1012 in only one direction and is configured to extend along the lumen inside another tubular conduit (not shown). To help hold second section 1014 in the other conduit, the second section may have a plurality of radially outwardly extending prongs 1080 (e.g., of nitinol wire) that deform or penetrate the side wall of the conduit in which the second section is disposed. Prongs 1080 may be curved and/or barbed somewhat like fishing hooks to help them even more securely hold onto the tissue that they engage. Either or both sections 1012 and 1014 of connector 1010 may be balloon-expanded to help anchor that section to the associated conduit.

Figure 42:
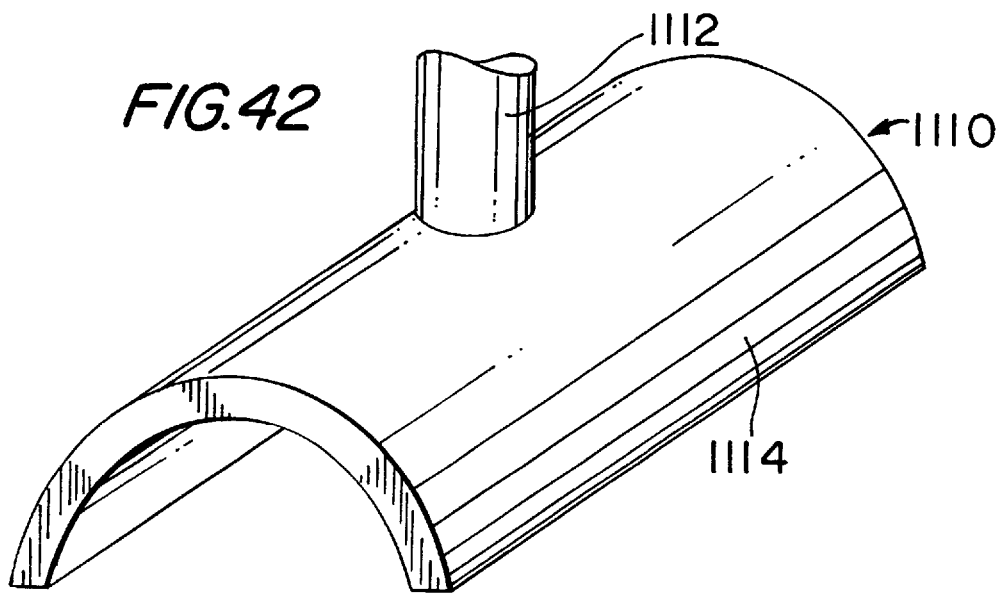
FIG. 42 is a simplified perspective view of still another illustrative embodiment of a connector in accordance with this invention.
Figure 43:
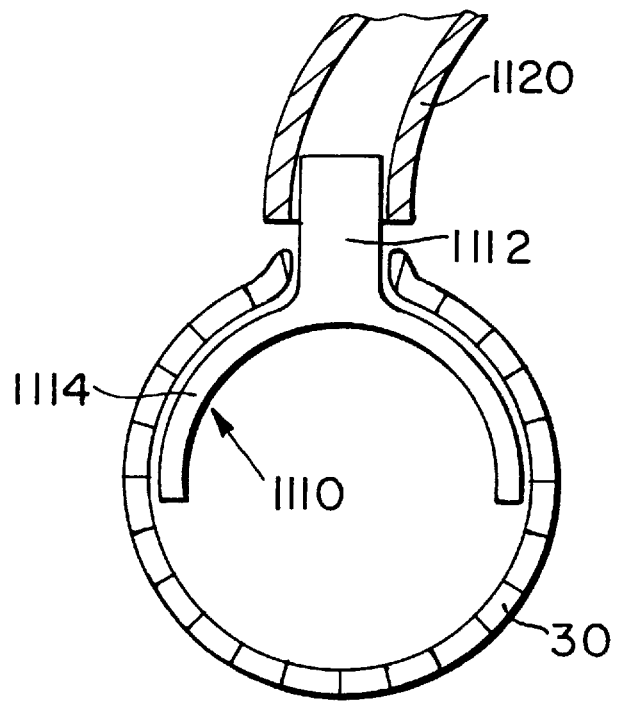
FIG. 43 is an elevational view of a connector of the type shown in FIG. 42 in use.

FIGS. 42 and 43 show another illustrative embodiment of a T-shaped connector 1110 which can be somewhat like the embodiment shown in FIGS. 15–17. The principal difference between this embodiment and the FIGS. 15–17 embodiment is that in connector 1110 the second section 1114 of the connector extends only part of the way around the inside of body conduit 30. This reduces the amount of connector material that is in contact with the interior surface of conduit 30. Reducing the circumferential extent of second section 1114 in this way may also facilitate delivery and installation of the connector. Second section 1114 may be perforated to facilitate changes of shape of that section for deployment of the connector. Graft conduit 1120 may be attached to first section 1112 in any suitable way (e.g., as described above in connection with other embodiments).

It will be understood that the forgoing is only illustrative of the principles of the invention, and that various modifications can be made by those skilled in the art without departing from the scope and spirit of the invention. For example, although particular materials have been mentioned for various components of the connectors of this invention, other materials can be used instead if desired.

The invention claimed is:

1. A structure for attachment to a tubular conduit for use in making a tubular connection to another conduit in a patient comprising:
    a substantially annular component having an initially relatively large circumference as compared to the circumference of the tubular conduit so that an axial portion of the tubular conduit can be inserted substantially coaxially into the annular component, the annular component being annularly compressible to a relatively small circumference, in which condition the annular component can substantially annularly engage the axial portion of the tubular conduit that has been inserted in the annular component.

2. The structure defined in claim 1 further comprising a plurality of prongs extending radially inwardly from the annular component.

3. The structure defined in claim 2 wherein the prongs are configured to penetrate the axial portion of the tubular conduit that has been inserted in the annular component when the annular component is compressed to the relatively small circumference.

4. The structure defined in claim 1 wherein the annular component comprises:
    axial portions that overlap one another in the radial direction, the extent of said axial portions increasing in the circumferential direction when the annular component is compressed to the relatively small circumference.

5. The structure defined in claim 1 wherein the annular component comprises:
    initially circumferentially spaced latching elements for latching together and holding the annular component in the relatively small circumference after the annular component has been compressed to the relatively small circumference.

6. The structure defined in claim 1 further comprising:
    an attachment structure connected adjacent an axial end of the annular component and configured to attach the annular component to the other conduit.

7. The structure defined in claim 6 wherein the attachment structure is configured for insertion into a lumen of the other conduit through an aperture in a side wall of the other conduit.

8. The structure defined in claim 7 wherein the attachment structure comprises a plurality of resilient fingers that are resiliently biased to extend radially out from the annular component.

9. The structure defined in claim 8 further comprising a second plurality of resilient fingers that are resiliently biased to extend radially out from the annular component, the second plurality of resilient fingers being axially spaced from the previously defined fingers so that the fingers in the second plurality remain outside the other conduit when the previously defined fingers are inside the lumen of the other conduit.

10. The structure defined in claim 7 wherein the attachment structure includes a tubular portion configured to be substantially coaxially disposed in the lumen of the other conduit.

11. The structure defined in claim 10 wherein the tubular portion extends transverse to a longitudinal axis of the annular component.

12. The structure defined in claim 11 wherein the tubular portion includes first and second tubular subportions which extends in diametrically opposite directions along an axis which is transverse to the longitudinal axis of the annular component.

13. The structure defined in claim 6 wherein the attachment structure is configured for attachment to an end portion of the other conduit.

14. The structure defined in claim 13 wherein the attachment structure comprises a second substantially annular component which is substantially coaxial with the annular component.

15. The structure defined in claim 14 wherein the second annular component has an initially relatively large circumference as compared to the circumference of the other conduit so that an axial portion of the other conduit can be inserted substantially coaxially into the second annular component, the second annular component being annularly compressible to a relatively small circumference, in which condition the second annular component can substantially annularly engage the axial portion of the other conduit that has been inserted in the second annular component.

16. The structure defined in claim 15 further comprising a plurality of prongs extending radially inwardly from the second annular component.

17. The structure defined in claim 16 wherein the prongs are configured to penetrate the axial portion of the other conduit that has been inserted in the second annular component when the second annular component is compressed to the relatively small circumference.

18. The structure defined in claim 15 further comprising:
    an axially compressible, tubular link between the annular component and the second annular component, the tubular link being substantially coaxial with the annular component and the second annular component.

* * * * *